US009895477B2

(12) United States Patent
Pudil et al.

(10) Patent No.: US 9,895,477 B2
(45) Date of Patent: Feb. 20, 2018

(54) DETACHABLE MODULE FOR RECHARGING SORBENT MATERIALS WITH OPTIONAL BYPASS

(71) Applicant: Medtronic, Inc., Minneapolis, MN (US)

(72) Inventors: Bryant J. Pudil, Plymouth, MN (US); Martin T. Gerber, Maple Grove, MN (US); David B. Lura, Maple Grove, MN (US); Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 484 days.

(21) Appl. No.: 14/261,651

(22) Filed: Apr. 25, 2014

(65) Prior Publication Data
US 2015/0306292 A1 Oct. 29, 2015
US 2017/0246367 A9 Aug. 31, 2017

Related U.S. Application Data

(60) Provisional application No. 61/909,372, filed on Nov. 26, 2013, provisional application No. 61/941,672, filed on Feb. 19, 2014.

(51) Int. Cl.
*A61M 1/14* (2006.01)
*A61M 1/16* (2006.01)
*B01J 20/00* (2006.01)

(52) U.S. Cl.
CPC ............ *A61M 1/14* (2013.01); *A61M 1/1696* (2013.01); *A61M 2205/3306* (2013.01); *A61M 2205/3334* (2013.01); *B01J 20/00* (2013.01)

(58) Field of Classification Search
None
See application file for complete search history.

(56) References Cited

U.S. PATENT DOCUMENTS

| 3,608,729 | A | 9/1971 | Haselden |
|---|---|---|---|
| 3,669,880 | A | 6/1972 | Marantz et al. |
| 3,776,819 | A | 12/1973 | Williams |
| 3,850,835 | A | 11/1974 | Marantz |
| 3,884,808 | A | 5/1975 | Scott |
| 3,902,490 | A | 9/1975 | Jacobsen et al. |
| 3,989,622 | A | 11/1976 | Marantz |
| 4,094,775 | A | 6/1978 | Mueller |
| 4,206,054 | A | 6/1980 | Moore |
| 4,209,392 | A | 6/1980 | Wallace |

(Continued)

FOREIGN PATENT DOCUMENTS

| CN | 104936633 | 9/2015 |
|---|---|---|
| EP | 2344220 B1 | 12/1999 |

(Continued)

OTHER PUBLICATIONS

PCT Application, PCT/US20013/020404, filed Jan. 4, 2013.

(Continued)

*Primary Examiner* — Richard Gurtowski

(57) ABSTRACT

A detachable module for optionally recharging sorbent materials, including zirconium phosphate, with an optional bypass and conduits for a sorbent cartridge. The sorbent cartridge can have one or more modules contained therein having connectors connecting each of the modules. One or more of the modules can be reusable and the sorbent materials therein recharged.

33 Claims, 7 Drawing Sheets

(56) References Cited

U.S. PATENT DOCUMENTS

| | | |
|---|---|---|
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,684,460 A | 8/1987 | Issautier |
| 5,230,702 A | 7/1993 | Lindsay et al. |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Andris Indriksons |
| 5,849,179 A | 12/1998 | Emerson et al. |
| 5,858,186 A | 1/1999 | Glass |
| 5,944,684 A | 8/1999 | Roberts et al. |
| 6,036,858 A | 3/2000 | Carlsson |
| 6,114,176 A | 9/2000 | Edgson et al. |
| 6,126,831 A | 10/2000 | Goldau et al. |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,283 B2 | 4/2005 | Thompson |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg et al. |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi et al. |
| 7,544,300 B2 | 6/2009 | Brugger et al. |
| 7,544,737 B2 | 6/2009 | Poss et al. |
| 7,563,240 B2 | 7/2009 | Gross et al. |
| 7,566,432 B2 | 7/2009 | Wong |
| 7,597,806 B2 | 10/2009 | Uchi |
| 7,794,419 B2 | 7/2010 | Paolini et al. |
| 7,776,210 B2 | 8/2010 | Rosenbaum et al. |
| 7,850,635 B2 | 12/2010 | Polaschegg et al. |
| 7,922,686 B2 | 4/2011 | Childers et al. |
| 7,922,911 B2 | 4/2011 | Micheli |
| 7,947,179 B2 | 5/2011 | Rosenbaum et al. |
| 7,955,290 B2 | 6/2011 | Karoor et al. |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 11/2011 | Kelly et al. |
| 8,066,658 B2 | 11/2011 | Karoor et al. |
| 8,080,161 B2 | 12/2011 | Ding et al. |
| 8,087,303 B2 | 1/2012 | Beavis |
| 8,096,969 B2 | 1/2012 | Roberts et al. |
| 8,180,574 B2 | 5/2012 | Lo et al. |
| 8,187,250 B2 | 5/2012 | Roberts et al. |
| 8,197,439 B2 | 6/2012 | Wang et al. |
| 8,303,532 B2 | 11/2012 | Hamada et al. |
| 8,404,491 B2 | 3/2013 | Ding et al. |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 2001/0007931 A1 | 7/2001 | Blatter |
| 2002/0112609 A1 | 8/2002 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2004/0019312 A1 | 1/2004 | Childers et al. |
| 2004/0099593 A1 | 5/2004 | DePaolis |
| 2004/0147900 A1 | 7/2004 | Polaschegg |
| 2004/0168963 A1 | 9/2004 | King |
| 2004/0257409 A1 | 12/2004 | Cheok |
| 2005/0006296 A1 | 1/2005 | Sullivan |
| 2005/0113796 A1 | 5/2005 | Taylor |
| 2005/0150832 A1 | 7/2005 | Tsukamoto |
| 2005/0274658 A1 | 12/2005 | Rosenbaum et al. |
| 2006/0241543 A1 | 10/2006 | Gura |
| 2007/0007208 A1 | 1/2007 | Brugger et al. |
| 2007/0179431 A1 | 9/2007 | Roberts et al. |
| 2007/0213665 A1 | 9/2007 | Curtin |
| 2008/0006570 A1 | 1/2008 | Gura |
| 2008/0051696 A1 | 2/2008 | Curtin |
| 2008/0053905 A9 | 3/2008 | Brugger et al. |
| 2008/0217245 A1 | 9/2008 | Rambod |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0157877 A1 | 6/2009 | Baek |
| 2009/0216045 A1 | 8/2009 | Singh |
| 2009/0266358 A1 | 10/2009 | Sacristan Rock |
| 2010/0004588 A1 | 1/2010 | Yeh |
| 2010/0007838 A1 | 1/2010 | Fujimoto |
| 2010/0078381 A1 | 4/2010 | Merchant |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford et al. |
| 2010/0217181 A1 | 8/2010 | Roberts et al. |
| 2010/0224492 A1 | 9/2010 | Ding et al. |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0248017 A1 | 10/2012 | Beiriger |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0190885 A1 | 7/2014 | Meyer |
| 2014/0217028 A1 | 8/2014 | Pudil |
| 2014/0251908 A1 | 9/2014 | Ding |
| 2014/0326671 A1 | 11/2014 | Kelly |
| 2015/0057602 A1 | 2/2015 | Mason |
| 2015/0108609 A1 | 4/2015 | Kushida |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |

(56) References Cited

U.S. PATENT DOCUMENTS

2015/0367059 A1  12/2015  Gerber
2015/0367060 A1  12/2015  Gerber

FOREIGN PATENT DOCUMENTS

| | | |
|---|---|---|
| EP | 711182 B1 | 6/2003 |
| EP | 1592494 B1 | 6/2009 |
| EP | 2575827 A2 | 12/2010 |
| EP | 2576453 A2 | 12/2011 |
| EP | 1545652 B1 | 1/2013 |
| EP | 1345856 B1 | 3/2013 |
| WO | 9532010 A1 | 11/1995 |
| WO | 0185295 A2 | 11/2001 |
| WO | 2002043859 | 6/2002 |
| WO | 2003043677 A2 | 5/2003 |
| WO | 2003051422 A2 | 6/2003 |
| WO | 2004062710 A3 | 10/2004 |
| WO | 2005123230 A2 | 12/2005 |
| WO | 2008075951 A1 | 6/2008 |
| WO | 2007089855 A2 | 3/2009 |
| WO | 2009157877 A1 | 12/2009 |
| WO | 2009157878 A1 | 12/2009 |
| WO | 2010028860 A1 | 2/2010 |
| WO | 2010102190 A4 | 11/2010 |
| WO | 2010141949 | 12/2010 |
| WO | 2013019179 | 2/2013 |
| WO | 2013019179 A1 | 2/2013 |
| WO | 2013025957 | 2/2013 |
| WO | 2013027214 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | 2004064616 A2 | 8/2013 |
| WO | 2013028809 A3 | 11/2013 |
| WO | 2015142624 | 9/2015 |
| WO | 2015199764 | 12/2015 |

OTHER PUBLICATIONS

U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2014/065950 International Search Report and Written Opinion dated Feb. 24, 2015.
PCT/US2015/032492 International Search Report dated Nov. 19, 2015.
PCT/US2015/016270 International Search Report and Written Opinion dated Jun. 5, 2015.
PCT/US2015/016273 International Search Report and Written Opinion dated Jun. 9, 2015.
PCT/US2015/032492 Written Opinion dated Nov. 19, 2015.
PCT/US2015/020046 International Search Report and Written Opinion dated Jun. 29, 2015.
International Search Report from PCT/US2012/051946.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
Office Action in U.S. Appl. No. 14/269,589, dated Nov. 4, 2016.
Office Action in U.S. Appl. No. 13/586,824 dated Dec. 21, 2015.
Office Action in U.S. Appl. No. 13/586,824 dated Jun. 4, 2015.
PCT/US2015/020044 International Search Report Written Opinion dated Jun. 30, 2015.
PCT/US15/18587 International Preliminary Report on Patentability dated Jun. 6, 2016.
PCT/US2014/065950 International Preliminary Report on Patentability dated Oct. 28, 2015.
European Search Report for App. No. 15751391.2 dated Aug. 4, 2017.
Office Action for Chinese Application No. 2015/80009562.5 dated Jul. 3, 2017.
International Preliminary Report on Patentability for Application No. PCT/US2015/032492 dated Jun. 30, 2017.
International Preliminary Report on Patentability for Application No. PCT/US2015/016273 dated Feb. 19, 2016.

DETACHABLE MODULE FOR RECHARGING SORBENT MATERIALS WITH OPTIONAL BYPASS

The present application claims the benefit to provisional applications no. 61/941,672, filed Feb. 19, 2014; and provisional application no. 61/909,372, filed Nov. 26, 2013, and in which all prior applications are hereby incorporated-by-reference.

FIELD OF THE INVENTION

The invention relates to a detachable module for optionally recharging sorbent materials, including zirconium phosphate, with an optional bypass and conduits for a sorbent cartridge.

BACKGROUND

Dialysis involves the movement of blood through a dialyzer that has a semi-permeable membrane. At the same time, dialysate is circulated through the dialyzer on an opposite side of the semi-permeable membrane. In this way, toxins present in the blood stream of the patient pass through the membrane into the dialysate. In traditional dialysis, the spent dialysate is disposed of after passing through the dialyzer. This requires a large amount of source water to prepare the necessary dialysate. In sorbent dialysis, however, the spent dialysate is re-circulated through a sorbent cartridge. The sorbent cartridge contains layers of sorbent material which selectively remove specific toxins, or break down toxins, in the dialysate.

The advantage of sorbent dialysis is that a much lower amount of water is required. In four hours of traditional dialysis, up to 120 L of water may be required to generate the dialysate. By contrast, using sorbent dialysis, as little as 6 or 7 L of water may be necessary. Thus, the need for drains and a continuous source of purified water are eliminated, rendering the system portable.

One of the drawbacks of sorbent dialysis systems is the high cost. The materials used in sorbent cartridges can be expensive. Disposing of the cartridges after each use generates waste and drives up costs. Other known dialysate fluid circulation systems and apparatuses have separate housings where a first housing has a material capable of releasing sodium into dialysate fluid flowing through the first housing, and a second housing has a material capable of binding sodium ions from dialysate fluid flowing through the second housing. However, such systems cannot be formed into a single housing design, oftentimes require many liters of water, and may not be portable. The systems also do not provide for recharging some or all of the components of a sorbent cartridge that would allow reuse of specific components and enable lower long-term costs for operating such systems.

Hence, there is a need for a sorbent cartridge having a separation of materials within the sorbent cartridge into modules to allow for isolation of those materials. There is a need for a sorbent cartridge providing for isolation of one or more sorbent material to allow for cheaper or non-reusable materials to be discarded, while more expensive and reusable materials are recharged. There is a further need for a unitary sorbent cartridge having multiple discreet modules that can be easily connected and/or detachable from the unitary sorbent cartridge thereby facilitating the recharging and/or recycling of the sorbent materials and the sorbent cartridge while retaining a single unitary design. There is also a need for a sorbent cartridge having the features of reduced size and weight necessary for a portable dialysis machine. There is a need for a modular sorbent cartridge wherein the sorbent materials can be arranged within the modules of the cartridge to allow for isolation of particular materials or groups of materials. There is a further need for any one of the modules in the cartridge to be reusable or optionally detachable and re-attachable from the cartridge to allow any one of disposal, recycling or recharging of sorbent material within the module. There is a need for a sorbent cartridge having specific materials that can be recharged and allowing for disposal of less expensive materials.

SUMMARY OF THE INVENTION

The present invention relates to a sorbent cartridge. In any embodiment, the sorbent cartridge can have at least one reusable module having one or more connectors fluidly connectable with a fluid flow path or fluidly connectable to a second module.

In one embodiment, the sorbent cartridge can comprise at least one non-reusable module. In another embodiment, the at least one reusable module can contain sorbent material. In another embodiment, the at least one reusable module can contain multiple sorbent materials. In another embodiment, the at least one non-reusable module can contain sorbent material. In another embodiment the at least one non-reusable module can contain multiple sorbent materials.

In another embodiment, at least one module can be in fluid communication or be a part of a controlled compliant dialysis circuit. In another embodiment, the at least one reusable module can be connected with at least one other either reusable or non-reusable module. In another embodiment, the at least one reusable module can be detachable from the sorbent cartridge.

In one embodiment, the connectors can be selected from quick-connect, twist-lock, push-on, or threaded fittings. In one embodiment, the one or more connectors can comprise a length of tubing and a valve assembly.

In one embodiment, a connector can include an access point tor a sensor. In one embodiment, a dialysis machine can comprise a connector. In one embodiment the sorbent material can be selected from a group comprising zirconium phosphate, hydrous zirconium oxide, activated carbon, alumina, urease and ion exchange resin. In any embodiment, the ion-exchange resin can be selected to only remove calcium and magnesium ions by using a chelating ion exchange resin.

In one embodiment, the flow path can flow in a direction through a first module, through a connector, and then through a second module. In another embodiment, the flow path can flow in a direction through a first module, through a connector, through a second module, through a second connector and then through a third module. In another embodiment, a bypass flow path can divert flow from a first module to a third module. In any embodiment, a plurality of modules is contemplated including four or more modules.

In another embodiment, the flow can be diverted by a bypass flow path using a valve assembly positioned on a connector. In one embodiment, the valve assembly can be positioned on a connector after the first module and before the second module. In another embodiment, the valve assembly can be positioned on a connector after the second module and before the third module.

In one embodiment, a recharger can be positioned on the bypass flow path.

In any embodiment, a connector can connect in fluid communication any one or more of the modules of the invention to a recharger.

In another embodiment the first module can contain hydrous zirconium oxide, alumina, urease and activated carbon, and the second module can contain zirconium phosphate.

In another embodiment, the first module can contain hydrous zirconium oxide, alumina, urease, zirconium phosphate and activated carbon, and the second module can contain zirconium phosphate. The respective layers can be formed into any combination of layers without restriction.

In another embodiment, the first module can contain hydrous zirconium oxide, alumina, urease, ion exchange resin and activated carbon, and the second module can contain zirconium phosphate. The respective layers can be formed into any combination of layers without restriction.

In another embodiment, the first module can contain alumina, urease, zirconium phosphate and activated carbon, and the second module can contain zirconium phosphate and hydrous zirconium oxide. The respective layers can be formed into any combination of layers without restriction.

In another embodiment, the first module can contain hydrous zirconium oxide, alumina, urease and activated carbon, and the second module can contain zirconium phosphate and ion exchange resin. The respective layers can be formed into any combination of layers without restriction.

In another embodiment, the first module can contain alumina, urease and activated carbon, and the second module can contain zirconium phosphate, ion exchange resin and hydrous zirconium oxide. The respective layers can be formed into any combination of layers without restriction.

In another embodiment, the first module can contain activated carbon, the second module can contain alumina and urease, and the third module can contain zirconium phosphate, ion exchange resin and hydrous zirconium oxide. The respective layers can be formed into any combination of layers without restriction.

In another embodiment, the first module can contain activated carbon, alumina, urease and hydrous zirconium oxide, the second module can contain zirconium phosphate, and the third module can contain zirconium phosphate and activated carbon. The respective layers can be formed into any combination of layers without restriction.

In another embodiment, the first module can contain activated carbon, the second module can contain alumina and urease, and the third module can contain zirconium phosphate, ion exchange resin and hydrous zirconium oxide. The respective layers can be formed into any combination of layers without restriction.

In one embodiment, the non-reusable module or modules can be disposable. In another embodiment, the reusable module or modules can be recyclable and/or recharged.

In another embodiment, at least one of the modules can have a barcode or other identification system. In one embodiment, two or more sorbent materials may be mixed together.

The invention is also directed to a method of recycling a reusable module. In one embodiment, the method can comprise the steps of disconnecting a reusable module from connectors connecting the reusable module to a non-reusable module, a bypass line and/or a wash line; removing the reusable module from a sorbent cartridge; emptying sorbent material from the reusable module; refilling the reusable module with new sorbent material; and reconnecting the reusable module to the connectors in the sorbent cartridge.

The invention is also directed to a method of replacing a detachable module that can be optionally reusable. In one embodiment, the method can comprise the steps of disconnecting a detachable module from connectors connecting the detachable module to another module that can be optionally reusable, a bypass line and/or a wash line; removing the detachable module from a sorbent cartridge; discarding the detachable module; and inserting and connecting a new module in the sorbent cartridge.

The invention is also directed to a method for recharging sorbent material within a reusable sorbent cartridge. In one embodiment, the method can comprise the steps of disconnecting a reusable module from connectors connecting the reusable module to another module, bypass line, and/or wash line; and connecting the reusable module to a recharger known to those of ordinary skill in the art. In one embodiment, the recharger can contain a fluid capable of recharging the sorbent material in the reusable module. The method can further comprise the steps of passing the fluid from the recharger through the reusable module; and reconnecting the reusable module to the connectors in the sorbent cartridge.

In one embodiment, the reusable module can contain zirconium phosphate, and the recharger can contain a solution comprising sodium and hydrogen ions. In one embodiment, the reusable module can also contain ion exchange resin. In one embodiment, the reusable module can also contain hydrous zirconium oxide and the recharger can also contain acetate ions.

In one embodiment, the recharger can contain a first fluid. In one embodiment, the method for recharging sorbent material can further comprise the steps of passing the first fluid through the reusable module; replacing the first fluid with a second fluid; and passing the second fluid through the reusable module.

In one embodiment, the reusable module can contain activated carbon and the recharger can contain heated water. In one embodiment, the reusable module can contain alumina and urease and the first fluid can be heated water; and the second fluid can contain urease.

In one embodiment, the valve assembly can be operated under control of a programmable controller or computer system to regulate flow into, out of, and between modules. In one embodiment, fluid flow through the valve assembly can be sensed by a photocell or other flow sensing and/or measuring apparatus. In one embodiment, the sorbent cartridge can comprise a control pump for circulating fluid in the fluid flow path.

In one embodiment, the sorbent cartridge can have multiple modules including any one of 2, 3, 4, or 5 modules. In any embodiment, the modules can be connected by any of quick-connect, twist-lock, push-on, or threaded fittings, or a length of tubing. In any embodiment, the modules can be used multiple times and/or recharged. In any embodiment having multiple modules, the number of times the multiple modules can be used or recharged can be different from each other.

DETAILED DESCRIPTION OF THE INVENTION

Figure 1:
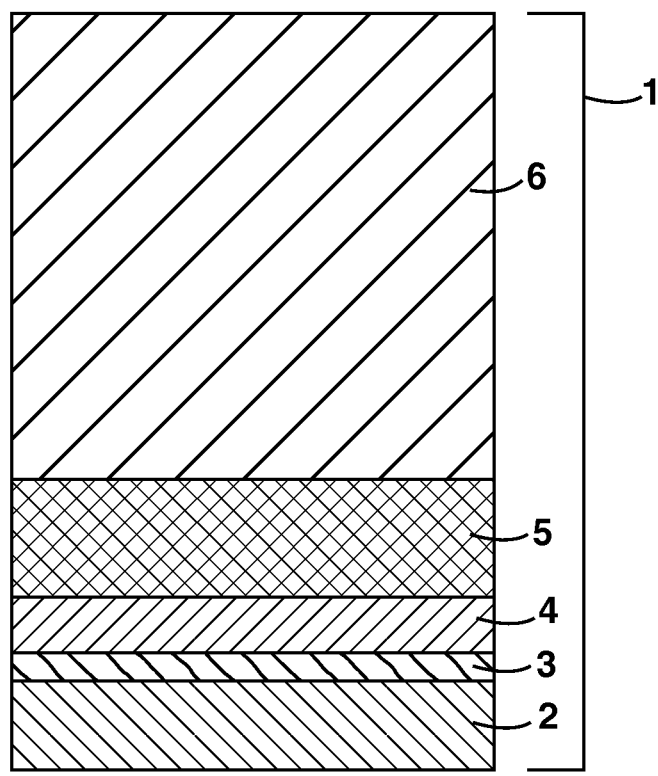
FIG. 1 shows a sorbent cartridge containing activated carbon, hydrous zirconium oxide, urease, alumina, and zirconium phosphate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

"Blow-out" refers to the process of passing a gas through a connection line or a module.

"Bypass line" refers to a line, connected to the main line, through which fluid or gas may alternatively flow.

The term "cartridge" refers to any container designed to contain a powder, liquid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "comprising" includes, but is not limited to, whatever follows the word "comprising." Thus, use of the term indicates that the listed elements are required or mandatory but that other elements are optional and may or may not be present.

A "connector" as used herein forms a fluid connection between two components wherein liquid or gas can flow from one of the components, through the connector, to another component. It will be understood that the connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "controlled compliant flow path", "controlled compliant dialysate flow path" and "controlled compliant solution flow path" refer to flow paths operating within a controlled compliant system having the characteristic of controlled compliance, or of being controlled compliant as defined herein.

The terms "controlled compliance" and "controlled compliant" describe the ability to actively control the transfer of fluid volume into or out of a compartment, flow path or circuit. In certain embodiments, the variable volume of fluid in a dialysate circuit or controlled compliant flow path expands and contracts via the control of one or more pumps in conjunction with one or more reservoirs. The volume of fluid in the system is generally constant (unless additional fluids are added to a reservoir from outside of the system) once the system is in operation if patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance," and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, the controlled compliant system can move fluids bi-directionally. In certain cases, the bi-directional fluid movement can be across a semi-permeable membrane either inside or outside a dialyzer. The bi-directional fluid flow can also occur across, through, or between vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

A "control pump" means an apparatus capable of moving fluid through a system at a specific rate. The term "control pump," can include for example an "ultrafiltrate pump," which is a pump that is operable to pump fluid bi-directionally to actively control the transfer of fluid volume into or out of a compartment or circuit.

A "control system" consists of combinations of components that act together to maintain a system to a desired set of performance specifications. The control system can use processors, memory and computer components configured to intemperate to maintain the desired performance specifications. It can also include fluid or gas control components, and solute control components as known within the art to maintain the performance specifications.

A "controller," "control unit," "processor," or "microprocessor" is a device which monitors and affects the operational conditions of a given system. The operational conditions are typically referred to as output variables of the system wherein the output variables can be affected by adjusting certain input variables.

A "degasser" is a component that is capable of removing dissolved and undissolved sasses from fluids.

The term "detachable" or "detached" relates to any component of the present invention that can be separated from a system, module, cartridge or any component of the invention. "Detachable" can also refer to a component that can be taken out of a larger system. In certain embodiments, the components can be detached with minimal time or effort, but in other instances can require additional effort. The detached component can be optionally reattached to the system, module, cartridge or other component. A detachable module can often be part of a reusable module.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

"Dialysate" is the fluid that passes through the dialyzer and does not pass through the membrane into the blood flow.

"Flow" refers to the movement of a liquid or a gas.

A "flow sensing apparatus" or "flow measuring apparatus" is an apparatus capable of measuring the flow of liquid or gas within a specific area.

A "fluid" is a liquid substance.

The term "fluid communication" refers to the ability of fluid or gas to move from one component or compartment to another within a system or the state of being connected, such that fluid or gas can move by pressure differences from one portion that is connected to another portion.

The term "fluidly connectable" refers to the ability of providing for the passage of fluid or gas from one point to another point. The two points can be within or between any one or more of compartments, modules, systems, components, and rechargers, all of any type.

"Infusate" is a solution of one or more salts for the adjustment of the composition of a dialysate.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. If will be understood that the designation of "first," "second," "third," etc. does not refer to the respective placement of the module in the direction of fluid or gas flow, and merely serves to distinguish one module from another unless otherwise indicated.

The term "non-reusable" refers to a component that cannot be reused in the component's current state. In certain instances, the term non-reusable can include the concept of being disposable, but is not necessarily limited to just being disposable.

An "operational line" is a line that directs fluid or gas in a path normally used, while the system is in normal operation.

The terms "pathway," "conveyance pathway," "fluid flow path," and "flow path" refer to the route through which a fluid or gas, such as dialysate or blood travels, or the route an inert gas travels.

A "photocell" is a sensor capable of measuring light or other electromagnetic radiation.

A "pressure valve" is a valve wherein, if the pressure of the fluid or gas passing the valve reaches a certain level, the valve will open to allow fluid or gas to pass through.

The term "pump" refers to any device that causes the movement of fluids or gases by the application of suction or pressure.

A "push-on fitting" is a fitting for connecting two components wherein the components may be connected by applying pressure to the base of the fitting attached to the components.

A "quick connect fitting" is a fitting for connecting two components wherein the male portion of the fitting contains flexible flanges extending outward with a portion on the end of the flange extending further outward, and the female portion of the fitting contains an internal ridge so that when connected; the outward extending portion of the flange sits under the ridge. By applying pressure, the flexible flange can be forced inward, past the ridge, enabling easy removal.

A "recharger" is a component that is capable of recharging spent sorbent material to or near its original state. A recharger may be part of the dialysis system or may be separate from the rest of the system. If the recharger is separate from the rest of the dialysis system, the term may include a separate facility where the spent sorbent material is sent to be returned to, or near, its original state.

"Recharging" refers to the process of treating spent sorbent material so as to put the sorbent material back in condition for use in sorbent dialysis. Upon a sorbent material undergoing "recharging," the sorbent material can then said to be "recharged."

The term "recyclable" refers to a material that can be reused.

"Reusable" refers in one instance to a sorbent material that can be used more than one time, possibly with treatment or recharging of the sorbent material between uses. Reusable may also refer to a sorbent cartridge that contains a sorbent material that can be recharged by recharging the sorbent material(s) contained within the sorbent cartridge.

A "sensor" is a component capable of determining the states of one or more variables in a system.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Sorbent material" is material capable of removing specific solutes from solution, such as urea.

"Spent dialysate" is a dialysate that has been contacted with blood through a dialysis membrane and contains one or more impurity, or waste species, or waste substance, such as urea.

"Tap water" refers to water obtained through piping from a water supply without additional treatment.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

A "threaded fitting" is a fitting for connecting two components wherein the male portion has a helical ridge wrapped around a cylinder, and the female portion is a cylindrical hole with internal helical ridges so that when the male portion is screwed into the female portion the two components are locked together.

A "twist-lock fitting" is a fitting for connecting two components wherein the male portion of the fitting contains a head with a length exceeding its width, the female portion of the fitting is a hole with a length that exceeds its width and is larger than the male portion, so that when the male portion is inserted into the female portion and either portion is twisted the two components become locked together.

"Uremic toxins" are toxins carried in the blood supply normally removed in the kidneys.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

A "wash line" is a line that directs fluid between a recharger and a module.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The terms "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "water source" refers to a source from which potable or not potable water can be obtained.

Sorbent Dialysis

Sorbent dialysis allows dialysis with a small volume of dialysate, creating many advantages. In sorbent dialysis, spent dialysate, containing toxins removed from the blood of the patient, is passed through a sorbent cartridge. The sorbent cartridge of the invention can contain sorbent materials that selectively remove specific toxins from the spent dialysate, either completely or by replacing them with non-toxic material. This process converts the spent dialysate into clean dialysate, which is then redirected back to the dialyzer.

One, non-limiting, exemplary sorbent cartridge is shown in FIG. 1. Spent dialysate can flow from the bottom of the sorbent cartridge 1 to the top of the cartridge. The first sorbent material the spent dialysate contacts can be activated carbon 2. Activated carbon will remove nonionic-toxins from the fluid by adsorption. Creatinine, glucose, uric acid, β2-microglobulin and other non-ionic toxins, except urea, can be adsorbed onto the activated carbon, removing those toxins from the fluid. Other non-ionic toxins will also be removed by the activated carbon. The fluid then continues through the sorbent cartridge to the zirconium oxide layer 3. The zirconium oxide layer 3 can remove phosphate and fluoride anions, exchanging them for acetate anions. The fluid can continue to move through the sorbent cartridge into the alumina/urease layer 4. Urease can catalyze the reaction of urea to form ammonia and carbon dioxide. The result of this is the formation of ammonium carbonate. The phosphate anions present in the fluid can also be exchanged for hydroxide ions on the alumina. As the fluid continues through the sorbent cartridge, it reaches alumina layer 5. Alumina layer 5 can remove any remaining phosphate ions from the fluid and helps retain urease within the sorbent cartridge. The last layer through which the fluid travels can lie the zirconium phosphate layer 6. In the zirconium phosphate layer 6, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the layer. The ratio of sodium to hydrogen ions released depends on the ratio originally present in the zirconium phosphate layer 6, and is therefore controllable. The result of the fluid passing through the sorbent cartridge 1 is that the fluid be regenerated and form dialysate that can be safely passed back through a dialyzer to a patient. In any embodiment, potassium, calcium and magnesium can be added to the clean dialysate to replace any ions which were removed by the sorbent cartridge. The ions can be added and or controlled via an infusate system that can be positioned on a section of the fluid flow path after the sorbent cartridge.

Figure 2:
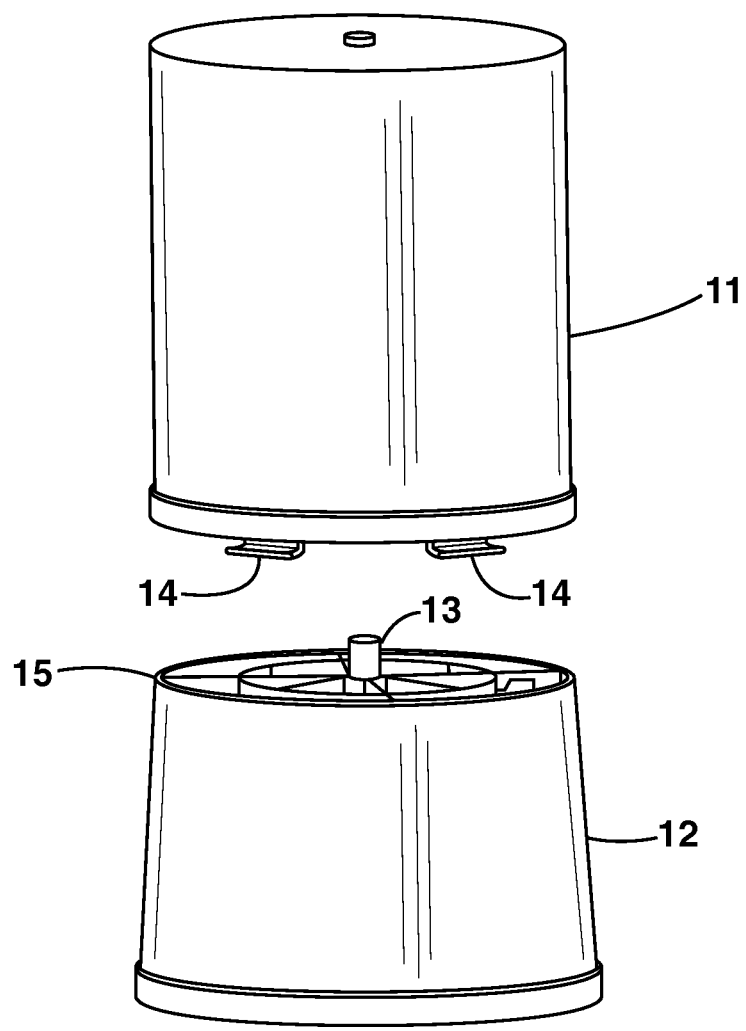
FIG. 2 shows a modular sorbent cartridge with two modules.

Given the cost of the sorbent cartridges and sorbent materials, it would be advantageous if parts of the cartridge could be reused. The present invention relates to a sorbent cartridge which includes at least one reusable module. In some embodiments, the reusable module 11 can be fluidly attached to a non-reusable module 12 by a connector 13 with the use of latches 14. The latches 14 can be integrally formed as part of the reusable module 11, non-reusable module 12, or may be a separate component that must be attached to either module as shown in FIG. 2. The latch members 14 can be mated to an annular connection ring 15 disposed on the circumference of module 12. One or more engagement members can be disposed inside the annular connection ring 15 to engage the latches 14 when positioned relative to each other using a radial motion. Such engagement can cause a rigid connection between the reusable module 11 and, the non-reusable module 12. Other known locking or fastening mechanisms known to those of ordinary skill that can effectuate rapid and effective connections, between two components are contemplated by the invention. Although only cylindrical modules are shown, it will be understood that modules of any shape such as rectangular, conical, triangular, etc. are contemplated by the present invention with a correspondent fastening mechanism. It will be understood that different combinations of reusable and non-reusable modules can be combined together. In certain embodiments, both modules may be reusable or both may be non-reusable. Moreover, any one of the modules can be detachable from each other or from a casing forming the body of the sorbent cartridge. The modules can be standardized components that are interchangeable with other modules and easily assembled. For example, the latches 14 in FIG. 2 allow for a simple, twist-lock between two modules. The twist lock allows for the modules to be connected to each other by an easy and rapid manual motion not requiring complex maneuvering of the modules. The connection, once made, can be resistant to inadvertent disengagement, but can also be readily disengaged when desired with a similar easy and rapid manual manipulation. For example, a force applied on the outside periphery of the modules near the latch, e.g. squeezing the module, can cause the latch member 14 to disengage from the engagement members. In other examples, the modules can be disengaged by simply rotating the modules relative to each other.

In certain embodiments, each module can function as a sorbent cartridge independently. In other embodiments, at least two modules can cooperate together when engaged to each other using, for example the latches 14 in FIG. 2 and being fluidly connected together to function as a sorbent cartridge. The advantage of such a modular design as described herein is that different sorbent materials can be dispersed between the at least two modules to allow for any particular sorbent or combination of sorbent materials to be detachable from a sorbent cartridge.

The connector 13 can be formed as part of the module and need not be a separate component that must be attached to the module 12. Rather, the connector 13 can be molded as part of the reusable module 12 and the non-reusable module 11. In other embodiments, the connector can be affixed by mechanical means, glued or rigidly interfaced to the modules 11 and 12. The connector can be a combination of female and male connectors on a module. For example, a female connector can be disposed on one module, and a male connector on the other to form one connector 13 (not shown). In any embodiment, the connector 13 allows fluid to flow into the non-reusable module 11, through the connector 13, into the reusable module 12. Alternatively, the connector 13 is not a part of either the non-reusable module 11 or reusable module 12 but can be a separate component such as tubing. It will be understood that the connector 13 is defined in its broadest sense and encompasses any fluid connection between two points.

One or more fluid connectors can be arranged between any module of the invention, and one or more such fluid connectors can be provided in any of the described configurations herein. For example, a reusable module can have any number of connectors such as 1, 2, 3, 4, 5, or more. The spacing and distribution of the fluid connectors on the module can be positioned to enable and/or increase flow of fluid between the modules. In one example, the fluid connectors can be spaced equidistant from each other or may be located axially or radially. Moreover, the sorbent cartridge may have one or more modules each having any number of connectors. In contrast to known sorbent cartridges having a unitary design in which sorbent materials are arranged in layers without any connectors between such layers, the fluid connectors of the present invention allow for controlled fluid or gas flow to any particular sorbent or combination of sorbent materials. The fluid connectors of the present invention also allow for any particular sorbent or combination of sorbent materials to be detachable from a sorbent cartridge. For example, a detachable module can be constructed with one or more sorbent materials. The detachable module can then be fluidly connected to the sorbent cartridge by fluid connectors. Such a configuration advantageously allows for separate treatment, recycling, or recharging of the sorbent or combination or mixture of sorbent materials not possible with known sorbent cartridges. In particular, known sorbent cartridges have all the sorbent materials being formed into layers or a plurality of sorbent materials being mixed without connectors in between such layers of one sorbent material, or mixtures of sorbent materials. Hence, it will be understood that the fluid connectors of the invention can be critical in that the connectors control the order of sorbent materials to which a fluid or gas is exposed to, the delivery of fluid or gas to a particular sorbent or combination of sorbent materials, and the flow and rate of flow of a fluid or gas to various sorbent materials, layers or sorbent materials, and combination or mixtures of sorbent materials.

It will be understood that the present invention is distinct from known dialysis systems requiring separate housings containing sorbent materials that do not form a unitary sorbent cartridge for ready attachment or insertion into a dialysis machine. A unitary sorbent cartridge of the present invention contains each one of the sorbent materials described herein including cation and anion exchange resins inside the sorbent cartridge. In other words, the cation and anion exchange resins (or other sorbent materials) are not separated into another housing outside the sorbent cartridge. Although the individual sorbent materials of the present invention may be separated into different detachable and/or reusable modules within the single sorbent cartridge wherein each module is connected by fluid connectors, the single sorbent cartridge design provides reduced size and weight that is not possible with the known dialysis systems having separate housings. The modules, as described herein, can also be further rigidly fixed to each other by latches and engagement members or any fixing or fastening mechanism known to those of ordinary skill in the art. Notably, the sorbent cartridge of the present invention can have all of the sorbent materials described herein including cation and anion exchange resins within a single unitary sorbent cartridge for convenient removal, service and monitoring. In particular, the sorbent cartridge can have a single compartmental design wherein all sorbent materials necessary for performing dialysis are contained within a single compartment. The sorbent cartridge can also have a modular design wherein the sorbent materials are dispersed across at least two different modules, which can be connected to form a unitary body. Once the at least two modules are connected together, the connected modules can form a sorbent cartridge to be fitted to a device or mechanism. Advantageously, the present sorbent cartridge therefore can be easier, to recycle, recharge, dispose of, service and remove from a dialysis machine. In certain embodiments, the unitary design can also provide for a compact design that can be used in a portable dialysis machine.

In any embodiment, the fluid connector can be a quick-connect, twist-lock, push-on, or threaded fitting. Other forms of such connection known to those of ordinary skill in the art are contemplated by the present invention. Additionally, the connector can comprise a length of tubing and a valve assembly. In certain embodiments, the connector can be manually assembled to connect any component or assembly of the invention. The connector can also be used to rigidly connect any one of the modules to a recharger as defined herein when a separate fastening mechanism is not provided.

In any embodiment of the invention, at least one module can be in fluid communication with a controlled compliant dialysis circuit as disclosed in U.S. patent application Ser. No. 13/565,733, the contents of which are incorporated herein in their entirety.

It will be understood that the connector provides for a fluid connection in its broadest sense and can include any type of tubing, fluid or gas passageway, or conduit between any one or more components of the invention.

Figure 3:
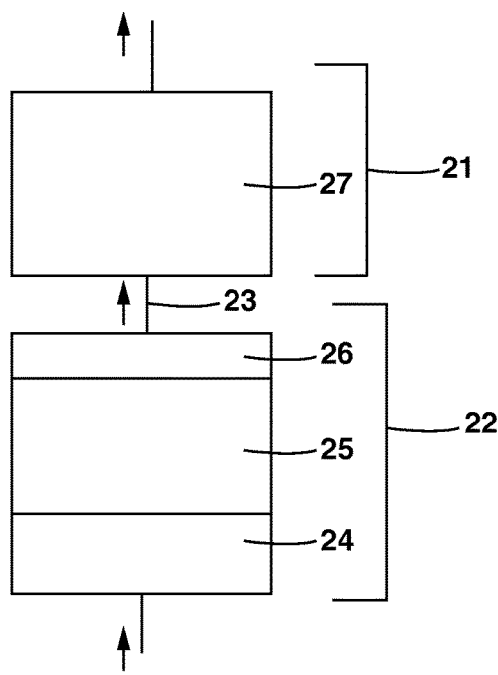
FIG. 3 shows a modular sorbent cartridge with two modules including activated carbon, alumina, urease, and zirconium oxide in the first module and zirconium phosphate in the second module.

One embodiment of the modular sorbent cartridge is shown in FIG. 3. The non-reusable module 22 of the sorbent cartridge can contain layers of activated carbon 24, alumina/urease 25, and hydrous zirconium oxide 26. The reusable module 21 contains zirconium phosphate 27.

After dialysis is complete, the zirconium phosphate layer 27 can contain ammonium, calcium, potassium and magnesium. The module 21 containing the zirconium phosphate may be removed, and the zirconium phosphate can be recharged. The reusable module 21 can be disconnected from the connectors 23 connecting the reusable module to the non-reusable module, bypass line and/or wash line. The reusable module 21 is then removed from the modular sorbent cartridge. This module can then be recharged, discarded and replaced, or alternatively, the sorbent material within the module can be removed and refilled. It will be understood that any one of the materials used in the present invention can be used multiple times. In such instances of multi-session use, the number of sessions that one component can be used, can be the same or different from the number of sessions that another component can be used. In one non-limiting example, a module containing urease may be used 2 times while another module containing zirconium phosphate can be used 3 times. In other cases, the module containing urease can be used 3 times, and the module containing zirconium phosphate used 2 times. It will be understood that there is no limitation on the numbers of uses for any multi-session use module as compared to another module used in the sorbent cartridge.

Figure 4:
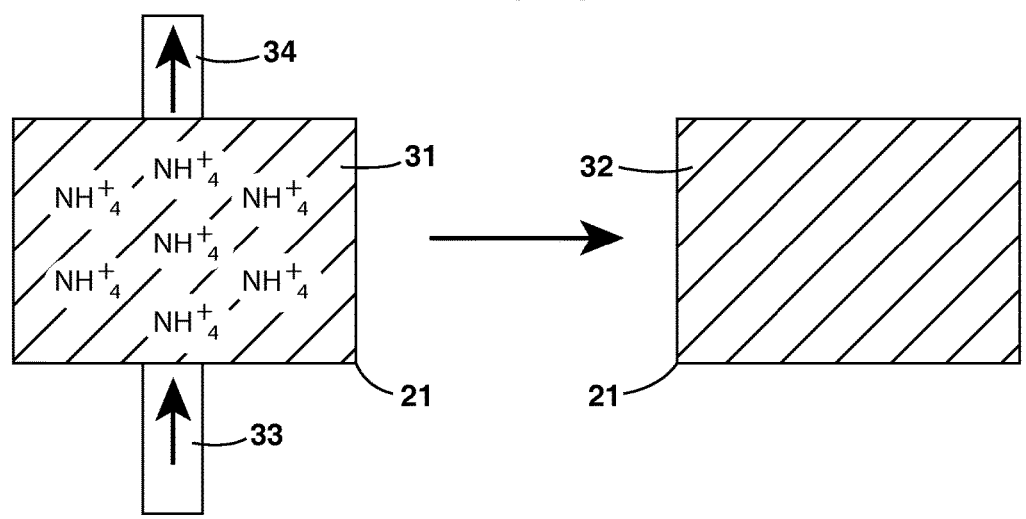
FIG. 4 shows a method for recharging the zirconium phosphate sorbent material.

The method of recharging the zirconium phosphate module is shown in FIG. 4. Wash fluid 33, containing sodium and hydrogen ions, can be passed through the reusable module 21, containing the used zirconium phosphate 31 with bound ammonium ions. This causes an exchange of ions, wherein hydrogen and sodium ions can replace the ammonium ions on the zirconium phosphate 31. The waste fluid exiting the module 34 thus contains the freed ammonium ions, with excess sodium and hydrogen ions. This process creates a recharged zirconium phosphate layer 32, containing sodium and hydrogen ions for a subsequent dialysis. In certain embodiments, a recharger can be used to restore spent sorbent material wherein the recharger contains fluid capable of restoring spent sorbent material to its original state.

Figure 5:
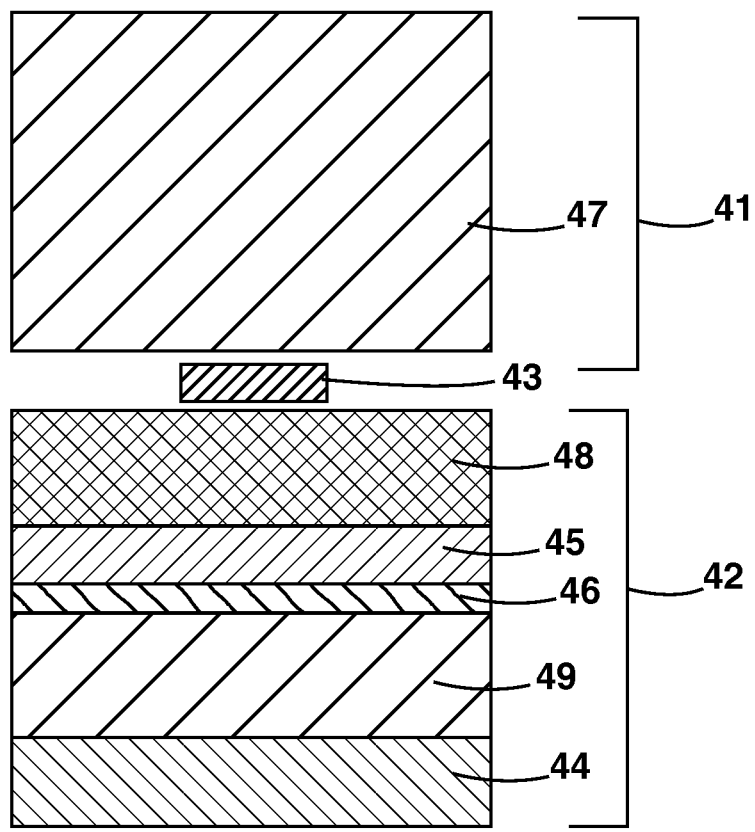
FIG. 5 shows a modular sorbent cartridge with two modules including activated carbon, zirconium phosphate, urease, alumina, and hydrous zirconium oxide in the first module and zirconium phosphate in the second module.

Because calcium and magnesium ions may be more difficult to remove from the zirconium phosphate, and therefore the zirconium phosphate may be more difficult to recharge, it may be advantageous to remove the calcium and magnesium in the first, non-reusable module, so that none of those ions need to be removed in the reusable zirconium phosphate module. Such an embodiment is in FIG. 5. Spent dialysate enters the first, non-reusable module 42 where the dialysate can first flow through a layer of activated carbon 44 to remove non-ionic uremic toxins. The dialysate can then enter into a first layer of zirconium phosphate 49. This layer can remove the calcium, magnesium and potassium from the fluid. Next the fluid enters the hydrous zirconium oxide layer 46, which removes the phosphate anions and exchanges them with acetate anions. The fluid can then enter the urease layer 45 and alumina layer 48, where the urea is converted to ammonium carbonate and any remaining phosphate ions are removed. In other embodiments of the non-reusable module, any arrangement of the activated carbon, zirconium phosphate, hydrous zirconium oxide layer, and urease and alumina layer is contemplated. For example, the dialysate can first flow through a first layer of zirconium phosphate, activated carbon, then the hydrous zirconium oxide layer, and then enter the urease layer and alumina layer. Alternatively, the dialysate can first flow through the hydrous zirconium oxide layer, then a first layer of zirconium phosphate, the activated carbon, then enter the urease layer and alumina layer. Still further, the dialysate can first flow through the urease layer and alumina layer, then the hydrous zirconium oxide layer, then a first layer of zirconium phosphate, and then the activated carbon. The fluid then flows through the connector 43, and into the second, reusable, sorbent module 41. This sorbent module can contain zirconium phosphate 47. Zirconium phosphate layer 47 can exchange the ammonium ions for sodium and hydrogen. Because the calcium, magnesium and potassium ions have already been removed by the first zirconium phosphate layer 49, this second layer 47 will not pick up those ions. Alter dialysis, the second module 41 will only contain zirconium phosphate hound to ammonium ions. As such, the dialysate may be easier to recharge.

In embodiments where the reusable module contains zirconium phosphate and ion-exchange resin, or zirconium phosphate and hydrous zirconium oxide, the module may be recharged in the same manner. The activated carbon layer of a reusable module can be recharged by passing a heated water solution through the module. The alumina/urease layers can be recharged by first passing heated water, or the solutions described above for recharging zirconium phosphate, through the layer, and then passing a solution containing urease through it.

Figure 6:
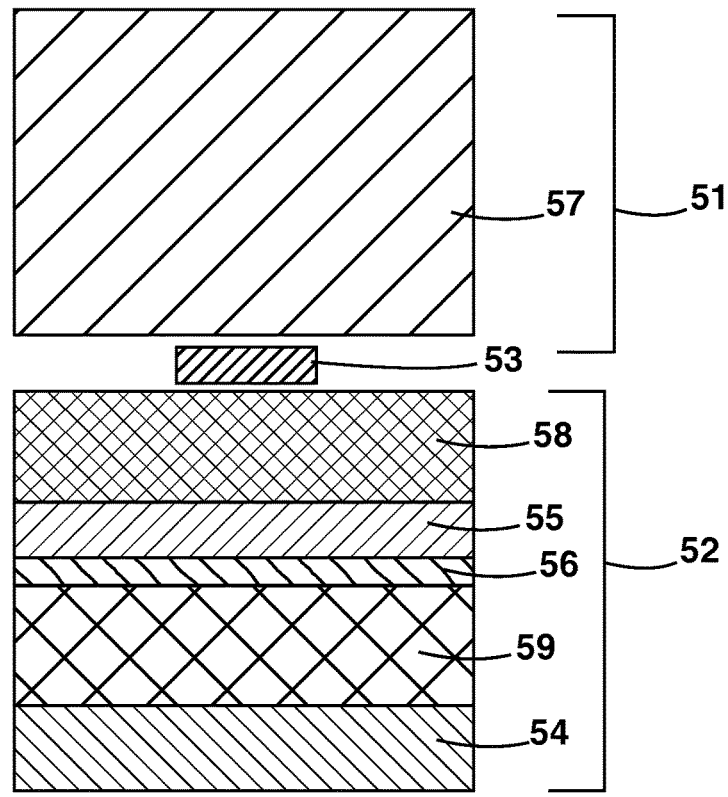
FIG. 6 shows a modular sorbent cartridge with two modules including activated carbon, ion exchange resin, alumina, urease, and hydrous zirconium oxide in the first module and zirconium phosphate in the second module.

Another non-limiting embodiment is shown in FIG. 6. Spent dialysate can enter the first, non-reusable; module 52 where it first flows through a layer of activated carbon 54 to remove non-ionic uremic toxins. It then enters into a layer of ion exchange resin 59. Ion exchange resin layer 59 can remove the calcium, magnesium and potassium from the fluid. Next the fluid can enter the hydrous zirconium oxide layer 56, which removes the phosphate anions and exchanges them with acetate anions. The fluid then enters the urease layer 55 and alumina layer 58, where the urea is converted to ammonium carbonate and any remaining phosphate ions are removed. In other embodiments of the first module, any arrangement of the activated carbon, ion exchange resin, hydrous zirconium oxide layer, and urease and alumina layer is contemplated. For example, the dialysate can first flow through an ion exchange resin, activated carbon, then the hydrous zirconium oxide layer, and then enter the urease layer and alumina layer. Alternatively, the dialysate can first flow through the hydrous zirconium oxide layer, then the ion exchange resin, the activated carbon, then enter the urease layer and alumina layer. Still further, the dialysate can first flow through the urease layer and alumina layer, then the hydrous zirconium oxide layer, then the ion exchange resin, and then the activated carbon. The fluid can then flow through the connector 53, and into the second, reusable, sorbent module 51. The sorbent module 51 contains zirconium phosphate 57. The zirconium phosphate layer 57 can exchange the ammonium ions for sodium and hydrogen. Because the calcium, magnesium and potassium ions have already been removed by the ion-exchange resin layer 59, the zirconium phosphate layer 57 will not pick up those ions. Alternatively, the ion-exchange resin 59 may be selected to only remove the calcium and magnesium ions, such as by using a chelating ion exchange resin. This can allow use of less of the ion exchange resin. If such a resin is used, the potassium will be removed by the zirconium phosphate 57. Potassium can be easier to remove from zirconium phosphate than calcium or magnesium.

One skilled in the art will recognize that different combinations of sorbent materials in both the reusable and non-reusable modules of the sorbent cartridge can be used without being beyond the scope of this invention. The sorbent materials described herein can be mixed together in any combination as shown in the specific embodiments of the invention.

Figure 7:
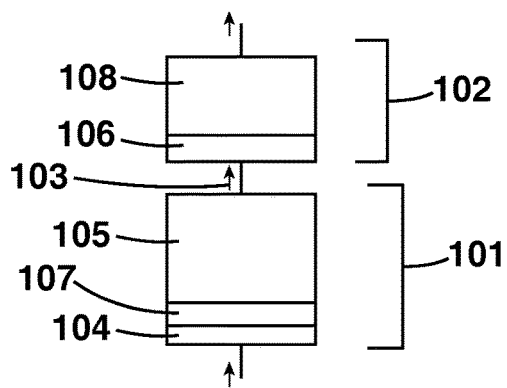
FIG. 7 shows a modular sorbent cartridge with two modules including activated carbon, alumina, urease, and zirconium phosphate in the first module and hydrous zirconium oxide and zirconium phosphate in the second module.

In any embodiment, the sorbent cartridge can be removed from a dialysis system. The sorbent cartridge once removed can be separated into one or more modules to be recharged, disposed of, or recycled. For example, FIG. 7 shows an embodiment wherein the reusable module contains both hydrous zirconium oxide and zirconium phosphate. The spent dialysate can enter the first module 101. The spent dialysate can first pass through the activated carbon layer 104. The spent dialysate can next pass through a first layer of zirconium phosphate 107, which removes the potassium, calcium and magnesium from the dialysate. Next the spent dialysate can moves through the alumina/urease layer 105. The fluid can then pass through the connector 103, and into the second module 102. The second module 102 contains a hydrous zirconium oxide layer 106, and a second zirconium phosphate layer 108, which removes the ammonium ions from the fluid. After dialysis, the reusable module 102 containing the hydrous zirconium oxide and zirconium phosphate can be recharged, discarded, or the sorbent material removed and new material added.

Figure 8:
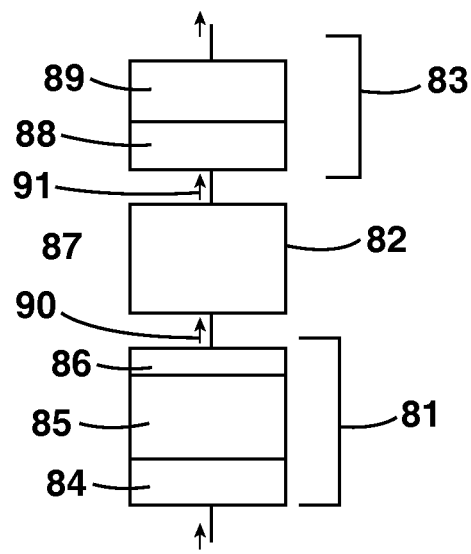
FIG. 8 shows a modular sorbent cartridge with three modules including activated carbon, alumina, urease, and hydrous zirconium oxide in the first module, zirconium phosphate in the second module, and zirconium phosphate and activated carbon in the third module.

One skilled in the art will realize that embodiments can be included that involve the sorbent materials being mixed within the module, as opposed to arranging the materials in layers. Such mixing of the sorbent materials can be performed interspersing the sorbent materials in a single layer by any method known to those of skill in the art. The modular sorbent cartridges in this invention are not limited to having two modules. Any number of modules may be utilized in this invention. A three module sorbent cartridge is shown in FIG. 8. The first module 81 contains a layer of activated carbon 84, a layer of alumina/urease 85, and a layer of hydrous zirconium oxide 86. The described layers can also be mixed together rather than being provided in layers. In other embodiments of the first module of a three module sorbent cartridge, any arrangement of the activated carbon, hydrous zirconium oxide layer, and urease and alumina layer is contemplated. For example, the dialysate can first flow through activated carbon, then the hydrous zirconium oxide layer, and then enter the urease layer and alumina layer. Alternatively, the dialysate can first flow through the hydrous zirconium oxide layer, then the activated carbon, then enter the urease layer and alumina layer. Still further, the dialysate can first flow through the urease layer and alumina layer, then the hydrous zirconium oxide layer, and then the activated carbon. Again, the described arrangements include not just layers, but also intermixed sorbent materials. The fluid, after passing through these layers, passes through a first connector 90, and into the second module 82. This second module 82 can contain zirconium phosphate 87. The fluid can then pass through a second connector 91, and enter a third module 83. This third module can contain a second layer of zirconium phosphate 88, and a second layer of activated carbon 89 for final purification before passing out of the sorbent cartridge. In other embodiments of the third module of a three module sorbent cartridge, any arrangement of the activated carbon and the second layer of zirconium phosphate are contemplated. For example, the dialysate can first flow through activated carbon and then the second layer of zirconium phosphate. It will be understood that any number of modules can be configured in the present invention. For example, a sorbent cartridge having four, five, six, seven, or more modules is contemplated by the invention. It will be understood that the described arrangements include not just layers, but also the sorbent materials being intermixed.

As each layer of sorbent material within the modular sorbent cartridge may be recharged, a cartridge is possible where all of the modules are reusable. It is still advantageous to utilize separate modules for the sorbent materials in order to direct the correct recharging solution through the correct module, and because different sorbent materials may need to be replaced more often than others.

Because the ability for the zirconium phosphate layer to bind ammonium ions is finite, while the capacity of the urease layer to break down urea into ammonia is not, the capacity of the zirconium phosphate layer may be exceeded. In such a case, excess ammonium ions can be caused to pass through the sorbent cartridge and remain in the dialysate. To protect patient safety, once ammonia breakthrough has occurred, either dialysis session can be stopped or at least urease can be prevented from catalyzing the conversion of urea to ammonia.

Figure 9:
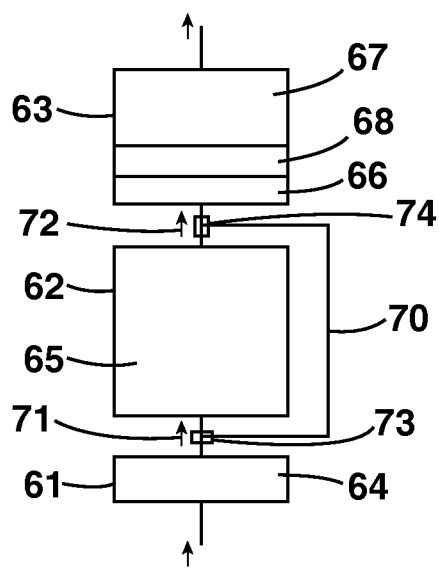
FIG. 9 shows a modular sorbent cartridge with three modules including activated carbon in the first module, alumina and urease in the second module, and ion-exchange resin, zirconium phosphate, and hydrous zirconium oxide in the third module, with an optional bypass line to direct fluid from the first to the third modules.

FIG. 9 shows a three-module sorbent cartridge that can allow bypass of the alumina/urease layer in the case of ammonia breakthrough. Ammonia breakthrough can occur when the capacity of the zirconium phosphate layer to exchange ammonium ion is exceeded. In the event of ammonia breakthrough, the spent dialysate can enter the first module 61, which contains the activated carbon layer 64. The spent dialysate then passes through a first connector 71, and by-pass flow valve 73. In normal operation, the flow valve 73 can be set to allow the fluid to pass into the second module 62. The second module can contain alumina/urease layer 65, which catalyzes the breakdown of urea into ammonium ions. The fluid then passes through the second connector 72, by the second valve 74, and into the third module 63. The third module can contain a hydrous zirconium oxide layer 66, ion-exchange resin 68, and zirconium phosphate layer 67. In other embodiments of the third module of a three module sorbent cartridge, any arrangement of the ion-exchange resin, hydrous zirconium oxide layer, and zirconium phosphate layer is contemplated. For example, the dialysate can first flow through ion-exchange resin, then the hydrous zirconium oxide layer, and then enter the zirconium phosphate layer. Alternatively, the dialysate can first flow through the hydrous zirconium oxide layer, then the ion-exchange resin, then enter zirconium phosphate layer. Still further, the dialysate can first flow through the zirconium phosphate layer, then the hydrous zirconium oxide layer, and then the ion-exchange resin. Again, the described arrangements include not just layers, but also intermixed sorbent materials. After passing through the third module, a regenerated dialysate can exit the sorbent cartridge. In the event of ammonia breakthrough, the first valve 73 can be set to redirect the fluid into bypass line 70. This line will cause the fluid not to enter the second module 62, and therefore the urea will not be broken down into ammonia in the alumina/urease layer. The fluid will instead be directed to the second valve 74, where the fluid enters the second connector 72, and then the third module 63. In this way dialysis may continue, while avoiding the creation of ammonia. The valve assembly can also include an access point for a sensor. The access point can be a portion of the valve assembly wherein a sensor can contact the fluid to take measurement data such as a flow or pressure reading. The form and construction of such access points contemplated by the present invention are those known to one of ordinary skill in the art.

Figure 10:
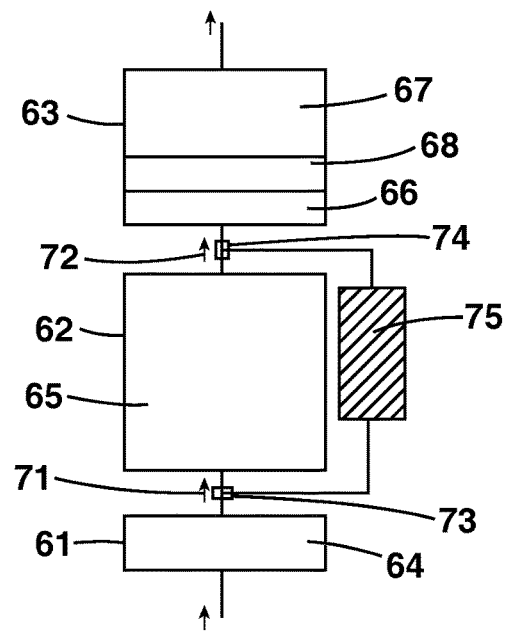
FIG. 10 shows a modular sorbent cartridge with three modules with an optional bypass line connected to another component such as a recharger.

FIG. 10 shows an alternative embodiment to the sorbent cartridge shown in FIG. 9 wherein a first connector 71 and a flow valve 73 bypass flow through the second module 62 to a component 75. The component 75 can be a recharger used to recharge or clean the second module 62 while attached to the sorbent cartridge. In other embodiments, the component 75 can be a container storing a fluid such as a wash fluid or recharging fluid. In still other embodiments, the component 75 can be pump for pumping fluid. Upon passing through the component 75, fluid can return through the second connector 72 via the second valve 74, and into the third module 63. In some embodiments, the component 75 can be removed after a period of time and fluid allowed to flow the third module 63 through the bypass first connector 72 and a flow valve 74. The component 75 can be reversibly attached and detached as necessary.

Figure 11:
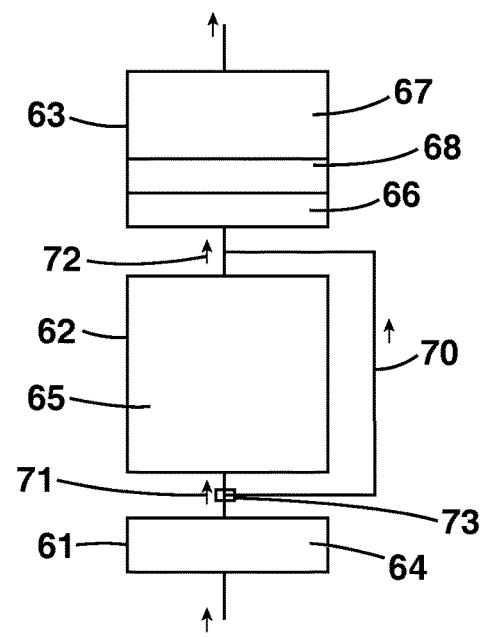
FIG. 11 shows a modular sorbent cartridge with three modules and an optional bypass line to direct fluid from the first to the third modules.

In an alternative to the embodiments shown in FIGS. 9 and 10, the bypass feature can be accomplished with a single three-way valve, as shown in FIG. 11. Valve 73, positioned on the first connector 71, can direct fluid from the first module 61 to either the second module 62 or bypass line 70. In other embodiments, a component may be added to bypass line 70, such as a recharger. In an alternative embodiment, the single valve may be positioned after the second module 62, on the second connector 72.

To make use of the modular sorbent cartridge easier, the valve assembly may be operated by a programmable controller or computer system that can be programmed to regulate flow through the valves and into and out of the modules. An optical sensor, photocell or other flow sensing apparatus may detect the flow of fluid through any two points in the sorbent cartridge. For example, an optical fluid flow device can be provided for measuring flow wherein the device includes an optical fluid pressure measuring device having sensors positioned in any one of the flow paths between the modules, in the connectors, or in the valve assemblies. Preferably, the sensors will be placed in a passageway defined between the modules. In certain embodiments, the optical fluid sensors can be connected to an interferometer associated with an opto-electronic demodulator which has an output signal representing the differential pressure between the two sensed areas. In other embodiments, a flow sensing apparatus can have a flow-responsive element projecting into a fluid flow path, and a position sensor associated with the element which detects a change in position of the flow responsive element in response to the fluid flow. The flow-responsive element can be made of a wide variety of materials having the desired properties known to those of ordinary skill in art.

It will be apparent to one skilled in the art that various combinations and/or modifications and variations can be made in the dialysis system depending upon the specific needs for operation. Features illustrated or described as being part of one embodiment may be used on another embodiment to yield a still further embodiment.

We claim:

1. A sorbent cartridge, comprising at least one rechargeable module containing at least one sorbent material, the rechargeable module rechargeable to restore a functional capacity of the at least one sorbent material, and having one or more connectors fluidly connectable to a second module; and the rechargeable module fluidly connectable to a recharger wherein the sorbent cartridge is reversibly attachable and detachable to the recharger.

2. The sorbent cartridge of claim 1, wherein the cartridge comprises at least one non-reusable module.

3. The sorbent cartridge of claim 1, wherein the at least one rechargeable module contains multiple sorbent materials.

4. The sorbent cartridge of claim 1, wherein the at least one module is part of a controlled compliant dialysis circuit.

5. The sorbent cartridge of claim 1, wherein the at least one-rechargeable module is detachable from the sorbent cartridge.

6. The sorbent cartridge of claim 1, wherein the at least one rechargeable module is connected with other modules, reusable or non-reusable, wherein the one or more connectors are selected from a group consisting of quick-connect, twist-lock, push-on, and threaded fittings.

7. The sorbent cartridge of claim 1, wherein the one or more connectors comprise a length of tubing and a valve assembly.

8. The sorbent cartridge of claim 1, wherein the sorbent material is selected from a group comprising zirconium phosphate, hydrous zirconium oxide, activated carbon, alumina, urease and ion exchange resin.

9. The sorbent cartridge of claim 1, wherein a fluid flow path flows in a direction through a first module, through a connector, and then through a second module.

10. The sorbent cartridge of claim 1, wherein a fluid flow path flows in a direction through a first module, through a connector, through a second module, through a connector, and then through a third module.

11. The sorbent cartridge of claim 1, wherein a bypass fluid flow path diverts flow from a first module to a third module.

12. The sorbent cartridge of claim 11, wherein the flow is diverted through the bypass fluid flow path using a valve assembly positioned on a connector.

13. The sorbent cartridge of claim 9, wherein the first module contains at least one material selected from the group consisting of hydrous zirconium oxide, alumina, urease, ion exchange resin, zirconium phosphate and activated carbon, and mixtures thereof; and the second module contains at least one material selected from the group consisting of zirconium phosphate, hydrous zirconium oxide, an ion exchange resin, and mixtures thereof.

14. The sorbent cartridge of claim 13 wherein at least the first module or second module contains the ion exchange resin and wherein the ion-exchange resin is a chelating ion exchange resin.

15. The sorbent cartridge of claim 10, wherein the first module contains at least one material selected from the group consisting of hydrous zirconium oxide, alumina, urease, ion exchange resin, and activated carbon, and mixtures thereof; and the second module contains at least one material selected from the group consisting of zirconium phosphate, hydrous zirconium oxide, ion exchange resin, alumina and urease, and mixtures thereof; and the third module contains at least one material selected from the group consisting of activated carbon, zirconium phosphate, ion exchange resin, and hydrous zirconium oxide, and mixtures thereof.

16. The sorbent cartridge of claim 2, wherein the non-reusable module is disposable after use.

17. The sorbent cartridge of claim 1, wherein at least one module has a barcode.

18. The sorbent cartridge of claim 7, wherein the one or more connectors include an access point for a sensor.

19. The sorbent cartridge of claim 1 wherein the one or more connectors is fluidly connectable to a bypass line and/or wash line.

20. The sorbent cartridge of claim 8, wherein the valve assembly is operated under control of a programmable controller or computer system to regulate flow into, out of, and between modules.

21. The sorbent cartridge of claim 7, wherein the valve assembly is operated under control of a programmable controller or computer system to regulate flow into, out of, and between modules.

22. The sorbent cartridge of claim 7, wherein fluid flow through the valve assembly is sensed by any one of a photocell, a flow sensor, or a measuring apparatus.

23. The sorbent cartridge of claim 1, wherein the sorbent cartridge is fluidly connectable to a control pump for circulating fluid in the fluid flow path.

24. The sorbent cartridge of claim 3, wherein the multiple sorbent materials are mixed together.

25. The sorbent cartridge of claim 11, wherein a recharger is positioned on the bypass flow path.

26. The sorbent cartridge of claim 12 wherein flow is diverted into the bypass flow path by use of a valve positioned on a connector after the first module and before the second module.

27. The sorbent cartridge of claim 12 wherein flow is diverted into the bypass flow path by use of a valve positioned on a connector after the second module and before the third module.

28. The sorbent cartridge of claim 10, wherein the first module contains urease, the second module contains zirconium phosphate, and the third module contains zirconium oxide.

29. The sorbent cartridge of claim 28, wherein the first module further comprises activated carbon.

30. The sorbent cartridge of claim 29, wherein the first module comprises a first layer of activated carbon, a second layer of urease downstream of the first layer, and a third layer of activated carbon downstream of the second layer.

31. The sorbent cartridge of claim 1, further comprising at least two rechargeable modules forming a unitary body.

32. The sorbent cartridge of claim 1, further comprising at least three rechargeable modules forming a unitary body.

33. The sorbent cartridge of claim 1, wherein the rechargeable module is a discreet component rigidly attachable to another module.

* * * * *